US00PP11672P

United States Patent [19]

Morrison

[11] Patent Number: Plant 11,672

[45] Date of Patent: Dec. 12, 2000

[54] HIBISCUS PLANT NAMED 'MORRISON-GILBERG (II)'

[75] Inventor: William L. Morrison, Park Ridge, Ill.

[73] Assignee: Gilberg Perennial Farms, Inc., Glencoe, Mo.

[21] Appl. No.: 09/008,220

[22] Filed: Jan. 16, 1998

[51] Int. Cl.[7] ..... A01H 5/00

[52] U.S. Cl. ..... Plt./257

[58] Field of Search ..... Plt./67.8, 257

[56] References Cited

U.S. PATENT DOCUMENTS

P.P. 9,838 3/1997 Bost ..... Plt./257

*Primary Examiner*—Howard J. Locker
*Assistant Examiner*—Kent L. Bell
*Attorney, Agent, or Firm*—Howell & Haferkamp

[57] ABSTRACT

A new and distinct hybrid variety of *Hibiscus moscheutos* cultivar, particularly distinguished by having flowers of from seven to twelve inches in diameter that are deep red, closely matching Pantone 215u. The flowers have fully overlapping petals. Pedicels about 3" and are distinctive in having a reddish color (Pantone 208U) that is more pronounced on the upper side; the back side is greenish-yellow. Distinguishing characteristics are constant and stable in asexually reproduced plants.

2 Drawing Sheets

BACKGROUND OF THE INVENTION

The present invention relates to a new and distinct variety of herbaceous perennial, more particularly to a hybrid variety of hibiscus.

BRIEF SUMMARY OF THE INVENTION

The new cultivar was developed by me as a progeny by cross-pollination in a garden in Park Ridge, Ill., a suburb of Chicago. The plant was originally produced as a seedling and has been successfully asexually reproduced by root crown division, under casual backyard gardening conditions. The plant has also been reproduced by vegetative reproduction, i.e., by tip and stem cuttings. The original seedling had parentage of 'Giant Red Plate' (unpatented) pollen parent and 'King Size' (unpatented) seed parent, both of which are cultivars of *Hibiscus moscheutos* grown and named by the inventor. The present cultivar is a herbaceous perennial; the stalks die back to ground level every winter and new stalks emerge in late spring. The trade name 'Rainier Red' has been coined for this cultivar, although the cultivar was neither marketed nor was its existence made public prior to the filing of the present U.S. Plant Patent application.

The present cultivar is distinguished by having flowers of from seven to twelve inches in diameter. These unusually large flowers can be cut and used for centerpiece displays, and last equally long with or without water. By comparison, *Hibiscus rosa-sinensis* (Chinese Hibiscus Rose of China) flowers are two to six inches in diameter, and *Hibiscus syriacus* (Rose-of-Sharon or Althea) flowers are three to six inches in diameter.

In its natural growth habit in the Chicago area, the present cultivar may be distinguished from both its pollen parent 'Giant Red Plate' and its seed parent 'King Size' in that the flowers of the present cultivar are much flatter than either parent, and the flowers have fully overlapping petals, a characteristic not found in either parent. In addition, typical flowers of the present cultivar are seven to twelve inches in diameter, whereas typical 'Giant Red Plate' flowers are from nine to ten inches in diameter, and 'King Size' flowers are typically nine inches in diameter and white in color. The 'Giant Red Plate' petals also have more pronounced ripples or undulations in the petals and the red color is not as intense as in the present cultivar. Moreover, the blooming period is longer for the present cultivar than for either of its parents, typically five to six weeks versus two to three weeks for its parents, depending upon weather.

The greatest number of flowers for the present cultivar was obtained in environments of half to full sun. The largest flowers were obtained at summer temperatures from 70 to 100 degrees Fahrenheit. Smaller flowers were observed to bloom at temperatures as low as 50 to 60 degrees Fahrenheit.

Reproduction by root crown division consistently produces plants with identical, stable characteristics. A further botanical description of the new variety follows. Distinguishing color characteristics are listed on the attached Plant Color Coding Sheet. The distinguishing characteristics listed thereon should not necessarily be assumed to be exhaustive. Although the listed characteristics are believed to be the primary distinguishing color characteristics of the cultivar, it is possible that others may become evident upon further observation and comparison with other cultivars. These descriptions were made from specimens reproduced and grown under casual backyard gardening conditions in suburban Chicago, Ill., and from specimens grown under greenhouse and outdoor gardening conditions in suburban St. Louis, Mo. Except as noted below, no differences were observed between the two locations, except that specimens were observed to grow somewhat faster and the blooming period is somewhat longer under warmer conditions, as one might expect for plant specimens of this species. In the following description, color references are made to the Pantone by Letraset Color Product Selector (© 1989 Pantone) except where general terms of ordinary significance are used.

BRIEF DESCRIPTION OF THE DRAWINGS

The accompanying drawings clearly depict the new variety, showing the colors as true as it is reasonably possible to obtain in colored reproductions of this type. Actual flower, leaf, sepal, and bud colors may differ from flower, leaf, sepal, and bud colors in the photographs due to light reflectance.

DETAILED BOTANICAL DESCRIPTION

Figure 1:
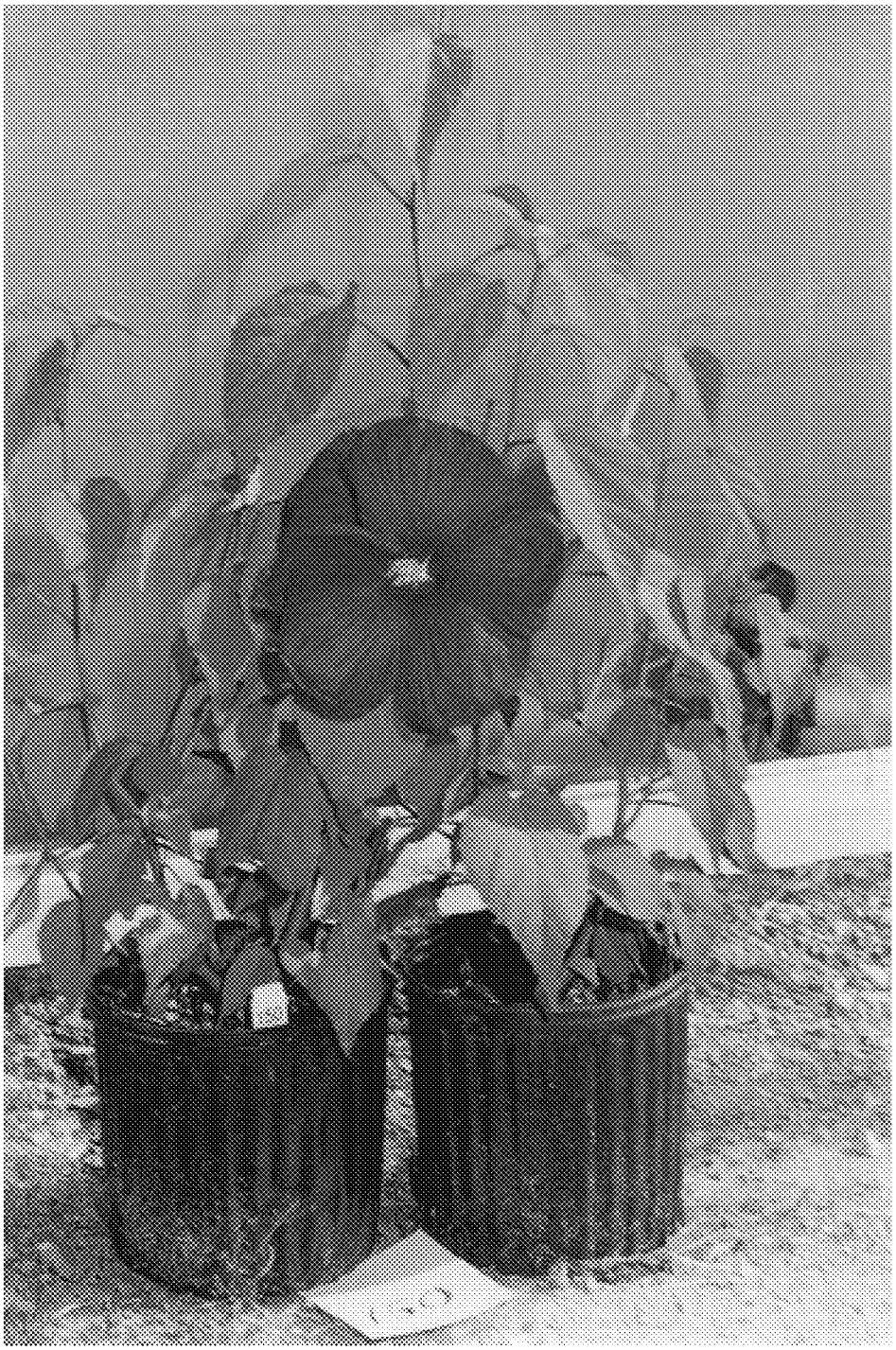
FIG. 1 depicts a side view of the *Hibiscus moscheutos,* 'Morrison-Gilberg (II)' cultivar of the present invention.
Figure 2:
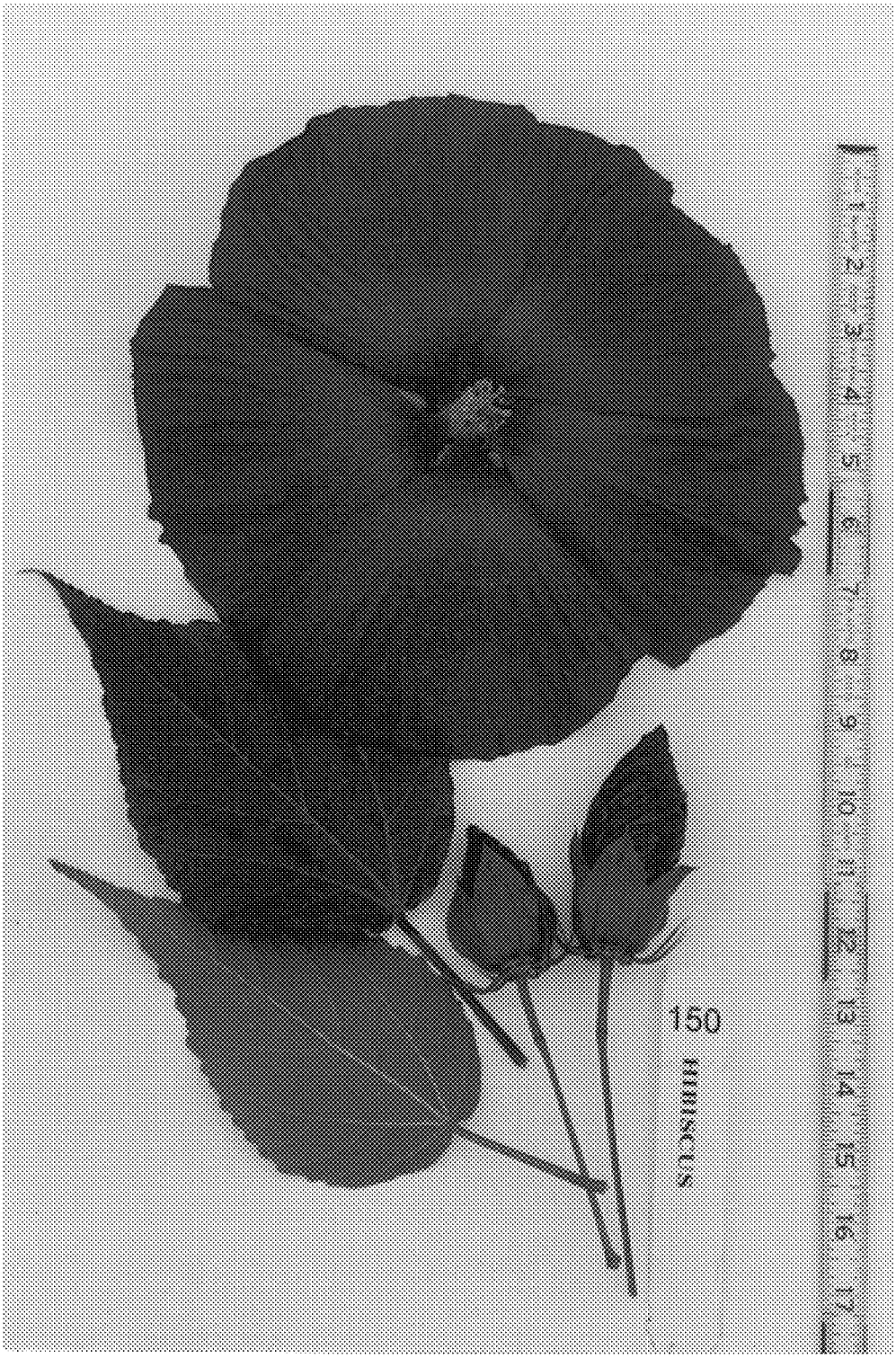
FIG. 2 is a close-up view of freshly cut portions of the *Hibiscus moscheutos,* 'Morrison-Gilberg (II)' cultivar of the present invention, showing the flower, leaves, and sepals surrounding flower buds in great detail.

Form: Numerous stalks grow upright from perennial roots.

Habit: Individual stalks with many leaves uniformly distributed on the stalks and numerous flowers bloom continuously. Rapid and strong stalk growth have flowers facing outward.

Productivity: Produces continuous new flower displays, vigorous and profuse.

Precocity: Elegant displays of flowers, each stalk displaying one new flower after another. On each stalk, as one flower closes and its petals fall off, a flower next to it and closer to the top of the stalk blooms, so that the displays appear to be continuous. The display periods may vary depending upon climate and the vigor of particular specimens.

Stalks: Mature presentations occur the first year. Strong and smooth skin covered, and hold many leaves and flowers securely. Staking is typically not required under normal full sun growing conditions. However, specimens grown in shaded sunlight produce stalks that are softer and that may require staking. New stalks emerge in May.

Temperature: Winter hardy during freezing winters. On 100 degree (Fahrenheit) days, the flowers bloom equally as they do during a mild day.

Insects: Negligible insect damage has occurred to date in any individual plant, even though no pesticides have been used, and no slugs have been observed on the plants.

Animals: Rodents, rabbits and squirrels have not been observed to bother the stalks or roots.

Rooting: The plants root easily without fertilizer and send out their roots quickly and securely.

Foliage: Large leaves evenly distributed vertically and horizontally on the stalks.

Leaves: Abundant and decorative in alternate order. Medium to dark green leaves with margin lengths of from three to eight inches generally in elongated heart form. Top color is Pantone 3435U. Bottom color is 556U. Typical leaves are about 7" to 8" long by about 4" to 5" at the widest point near the base. Shape is somewhat deltoid, with crenate margin. Tip is apiculate, base is rounded and slightly cordate, and venation is pinnate. Leaf texture is matte. Petioles from two to four and one-half inches. No stipules.

Stem color: Red stems (Pantone 200U and petioles (Pantone 202U). Pedicels about 3" and are distinctive in having a reddish color (Pantone 208U) that is more pronounced on the upper side; the back side is greenish-yellow.

Height: Mature plants are from three to five and one-half feet in height and about three to four feet in width.

Shape of plant at maturity: Rounded, almost globe-shaped.

The Flowers

Buds: Shaped like a pointed egg and very large one to two days before blooming. Can be over 3" in length just prior to opening. Typically about 3" long by about 1¼" to 1½" at its widest point. Color is Pantone 216U.

Blooming habit: Continuous and free blooming.

Petals: Two to six inches long, five per flower.

Diameter of flower: A distinguishing feature of the variety, flowers are from seven to twelve inches in diameter.

Shape: Circular and relatively flat with overlapping petals.

Number of flowers: Approximately 10–15 flowers per stalk in mature plants, with essentially flat appearance.

Filaments: Each of the approximately 15 filaments attaches to the large style projecting from the center of the flower. Approximately ⅛" to ¼" in length.

Stamens: Pink to red, very numerous, and extend from the style.

Pistil: Two to five inches long with the stamen and stigma attached. Color is yellow.

Stigma: Pink, with five pollen receptors.

Style: About two inches long, pink style supports the stigma.

Pollen: Yellow and plentiful.

Shape of petal: Overlapping and broadly obovate (almost reniform) recurved at the base to form a small green star of revealed calyx, with overall circular shape.

Texture: Central one-fourth satiny; outer three-fourths velvety.

Aspect of flower: Like fine kidskin in appearance and strongly self-supporting.

Color: Deep red, closely matching Pantone 215U . Constant and stable in asexually reproduced plants. Because of differences in texture across the surfaces of the petals, the petal at the base of the pistil may appear darker red (e.g., Pantone 216U) than the rest of the petal, producing the appearance of an eye. The darker appearance tends to be more pronounced in photographs than on flowers observed in natural light.

Calyx: Six sepals, medium green color.

Bractlets: About 1½", medium green. Same color as bracts, Pantone 583U.

Blooming period: Mid summer to frost with continuous color presentation. In suburban Chicago, typically about five to six weeks in August and September, depending on weather conditions. Blooms have been observed at least as early as July in St. Louis. Container plants produce flowers longer, on lateral stems, as the main stems are cut back and laterals emerge.

Lastingness of the bloom: Individual blooms allowed to remain on the plant last approximately 1–3 days per bloom, typically two full days. Individual flowers hold their shape for about a day after cutting with about 2 to 3 inches of stem, with or without water, if not exposed to wind and heat, which can cause them to wilt and fade quickly. However, if buds almost ready to open are cut with about one foot of stem, the cuttings may be kept in water for 1–3 days and will open almost normally.

Peduncle: Two to four inch stiff pedicels to support the flower during blooming and the seed pod formation later.

Fruit: Seeds produced, typical of the species.

Fragrance: Minimal.

Disease resistance: No disease problems have been noted on stalks, leaves or flowers.

Environmental conditions: The plants can stand drought or up to two inches of rainwater without adverse effects.

Winter dormancy: The plants lose their leaves at frost and stems die back to ground level.

Fertility: Midwest topsoil provides adequate nutrients without additional fertilizer.

Regularity of bearing: Consistent year-to-year flowering has been observed.

What is claimed is:

1. A new and distinct variety of *Hibiscus moscheutos* plant, as herein shown and described.

* * * * *